United States Patent [19]

Yao et al.

[11] 3,994,799
[45] Nov. 30, 1976

[54] BLOOD AND TISSUE DETOXIFICATION APPARATUS

[76] Inventors: Shang J. Yao, 5 Bayard Road - Apt. 920, Pittsburgh, Pa. 15213; Sidney K. Wolfson, 205 Buckingham Road, Pittsburgh, Pa. 15215

[22] Filed: Jan. 29, 1975

[21] Appl. No.: 545,169

Related U.S. Application Data

[60] Division of Ser. No. 352,070, April 17, 1973, Pat. No. 3,878,564, which is a continuation-in-part of Ser. No. 244,071, April 14, 1972, abandoned.

[52] U.S. Cl. ................................. 204/301; 3/1.1; 128/214 B; 204/263; 204/271; 204/DIG. 3; 204/DIG. 4; 210/321 A; 210/321 B
[51] Int. Cl.² .................................... B01D 13/02
[58] Field of Search ........... 204/151, 129, 130, 131, 204/263, 180 P, 271, 301, DIG. 3, DIG. 4; 128/214 B; 3/1, 1.1; 210/321 R, 321 A, 321 B

[56] References Cited
UNITED STATES PATENTS

| | | | |
|---|---|---|---|
| 3,353,539 | 11/1967 | Preston | 136/86 E X |
| 3,410,729 | 11/1968 | Manion | 136/86 E |
| 3,681,145 | 8/1972 | Kohmuller et al. | 136/86 R |
| 3,692,648 | 9/1972 | Matloff et al. | 204/129 |
| 3,769,090 | 10/1973 | Katz et al. | 136/86 R |
| 3,774,243 | 11/1973 | Ng et al. | 136/86 R X |
| 3,829,370 | 8/1974 | Bourat | 204/151 X |
| 3,837,922 | 9/1974 | Ng et al. | 136/86 R |

*Primary Examiner*—Arthur C. Prescott
*Attorney, Agent, or Firm*—Jacques M. Dulin

[57] ABSTRACT

Method and apparatus for blood and tissue detoxification by oxidation of excess undesirable or toxic substances such as ammonia, urea, creatinine, alanine, carbon monoxide, drug overdoses, uric acid, actone, aceto acetate and ethanol in an electrochemical cell which may be implanted or used in an extracorporeal shunt system. The cell may be hybridized with a battery to drive the cell under certain conditions, and the cell may be employed as part of a blood toxic substance level monitoring system. The invention is typified by the case where electrochemical cells convert oxygen and the enumerated toxic substances in the body fluids to harmless products such as $CO_2$, water and nitrogen which are easily dissipated. The cells have hydrophobic cathodes having a membrane thereover of silicone rubber, polyfluorocarbon, polycarbonate, and copolymers thereof which permit diffusion of oxygen therethrough. The anodes may be either hydrophilic or hydrophobic, the former employing a membrane thereover of cellulose or a cation resin and the latter a silicone rubber toxic substance- diffusible membrane. The electrodes are separated by an anion exchange membrane, or inorganic matrix edge-impregnated with a cation exchange membrane. The cells are simple of construction, and typically thin, wafer-like in form which permits ease of implantation at any desired location in the body. In its broadest aspect, the invention involves the use of electromechanical cells in the manner of artificial organs to remove toxic substances the body is unable to metabolize.

27 Claims, 20 Drawing Figures

BLOOD AND TISSUE DETOXIFICATION APPARATUS

CROSS REFERENCE TO RELATED APPLICATION

This is a division, of application Ser. No. 352,070 filed Apr. 17, 1973, now U.S. Pat. No. 3,878,564 which application Ser. No. 352,070 is a continuation-in-part of application Ser. No. 244,071 filed Apr. 14, 1972, now abandoned. The disclosure of each is hereby incorporated by reference herein.

FIELD

This invention relates to method and apparatus for removal of toxic or unwanted substances such as ammonia, urea and ethanol from blood, dialysate and body tissue fluids. More specifially, the invention is directed to electrochemical auto-oxidation cells such as one which employs ambient fluid oxygen levels to oxidize ammonium ions to nontoxic water and $N_2$, and urea to nontoxic $N_2$, $H_2O$ and $CO_2$, removable by natural homeostatic processes. The cells may be adapted for direct implantation into the patient's blood stream or body tissue spaces, or to be employed in an extracorporeal blood shunt or in combination with a dialysate unit. The cells may also be hybridized with a battery or employed as a monitor of ammonia or other reactant levels.

BACKGROUND

Chronic hepatic failure and acute ammonia intoxication are serious diseses involving abnormally high blood-ammonia levels. Acute alcoholic coma obviously results from markedly elevated tissue alcohol levels. Previous methods for treating patients having such diseases include: dietary protein restriction, antibiotic administration, hemedialysis, extracorporeal ion-exchange blood shunts, and finally, transplantation of donor liver. The blood shunt involves passing blood through an external shunt loaded with micro-capsules containing ion-exchange resins which remove the ammonia and replace it with sodium ions. As well as involving aseptic surgical techniques and providing only periodic relief, the external shunt may lead to high blood sodium levels.

Recent developments in methods for urea removal in hemodialysis involve the action of urease on urea with the release of large quantities of ammonia as a product. The presence of a high ammonia concentration in the dialysate rapidly leads to reverse dialysis of ammonia and marked increases in the patient's blood ammonia level. To prevent this from happening, the released ammonia is then either adsorbed or trapped by microencapsulated cation exchange resin [Chang, T.M.S., Semi-permeable Aqueous Microcapsules "Artificial Cells": With Emphasis on Experiments in an Extracorporeal Shunt System, Trans, Amer. Soc. Artif. Int. Organs, 12:13–19 (1966); Sparks, R. E., Solemme, R. M., Meier, P. M. Litt, M. H. and Lindan, O., Removal of Waste Metabolities in Uremia by Microencapsulated Reactants, Trans. Amer. Soc. Artif, Int. Organs, 15:353–58 (1969)], or by zirconium phosphate [Gordon, A., Greenbaum, M. A., Marantz, L. B., McArthur, M. and Maxwell, M. H., A Sorbent-based Low-Volume Recirculating Dialysate System Trans. Amer. Soc. Artif, Int. Organs, 15:347–52 (1969); Greenbaum, M. A. and Gordon, A., A. Regenerative Dialysis Supply System, Dial. Transpl., 1:18–30 (1972)]. The zirconium phosphate system also includes activated carbon and zirconium oxide and urease to convert urea in dialysate to ammonium carbonate. This system was developed by the Marquardt Co. in Van Nuys, California, under the trademark REDY. These systems have the advantage that a small volume of water (tap), which is recycled, can replace very large volumes of expensive dialysis fluid. The bulk of equipment is thus also markedly reduced. The major difficulty of this adsorption or ion exchange method is that the sorbent becomes saturated with ammonium ions during dialysis and cannot be regenerated in practice. The sorbent loaded cartridge needs to be repeatedly replaced. This becomes expensive and reduces one of the main potential advantages of the method.

Most of the above methods are short-range periodic treatments and are still in the experimental stage.

THE INVENTION

OBJECTS

It is therefore an object of the present invention to provide an automatic process for continuous removal of toxic substances from blood and tissue of patients having abnormally high levels of these substances.

It is also an object of this invention to provide an implantable device which operates continuously in the patient's body for the patient's life span.

It is another object of the invention to provide an implantable device which employs electrocatalysts to automatically and continously react with both oxygen and excess toxic substances such as ammonia present in the body fluids in the case of a hepatic disease patient or of other substances such as urea in different disease or toxic states as mentioned above.

It is another object of this invention to provide an implantable device to continuously measure the ammonia, urea or other toxic substance level in the tissues of a patient.

It is another object of this invention to provide a miniaturized hybrid system comprising an electrochemical cell utilizing the toxic substance in combination either with the toxic substance level measuring device or a battery, or both.

It is another object of this invention to provide an electrochemical system or extracorporeal shunt system for removal of excess toxic substances at higher rates than would result from spontaneous reaction.

It is another object of this invention to provide a novel cell of the type described which is adapted to be implanted in the body of a patient, and capable of using ambient body fluid oxygen levels for oxidizing the body toxic substance(s) to nontoxic products.

It is another object of this invention to provide an extracorporeal shunt system which rapidly oxidizes toxic substances such as ammonia or urea to harmless nontoxic byproducts, such as nitrogen and water which are removed by homeostatic processes.

It is another object of this invention to provide an extracorporeal shunt system which rapidly oxidizes, electro-chemically, dialysate ammonia generated by the action of urease on urea in hemodialysis to harmless nontoxic nitrogen and water which can be reabsorbed by the patient and removed by homeostatic processes.

It is another object of this invention to position the electrochemical cell in a closed dialysis loop after the urease reactor.

It is another object to provide an implantable cell which is in situ with a urease reactor whereby a urease microencapsulated material is actually packed into the blood space between electrodes so that the electrodes are in contact with a higher concentration of ammonia due to the close proximity of the urease capsules where ammonia is generated.

It is another object of this invention to provide an extracorporeal shunt system which directly and rapidly oxidizes dialysate-urea in renal dialysis to harmless nontoxic carbon dioxide, nitrogen and water, which are removed by homeostatic processes. This is accomplished without prior conversion of the dialysate-urea to $NH_3$ by urease.

Still other and further objects of this invention will be evident from the detailed description which follows.

THE FIGURES

The detailed description has reference to the following figures which are meant as illustrative and not limiting, and which refer to the specific instance of an ammonia or urea detoxifying cell which could also be used equally as well as an ethanol etc. detoxifying cell in most of its embodiments. With minor modifications in material, it could describe similar systems to detoxify other substances such as uric acid, digitalis, methanol, barbiturates, etc., as described above.

SUMMARY

The invention comprises providing an electrochemical cell system in which toxic substances are oxidizable reactants and oxygen air or other reducible constituents such as $NO_3^{-1}$, $PO_4^{-3}$, $SO_4^{-2}$ is an oxidant. The description will particularly relate to the specific situation in which blood or tissue ammonia or urea is the toxic substance, but the invention is not restricted to this example. Both the ammonia or urea and the oxygen are supplied continuously by blood or by tissue fluid. The cell employs electrocatalysts to automatically and continuously react with the oxygen, and excess ammonia in a typical hepatic disease patient, or urea in the case of kidney failure, to oxidize the ammonia or urea to nitrogen, carbon dioxide and water. These reaction products are nontoxic and are removed by homeostatic processes natural to the body. A high level of power output is not essential to the operation of the cell system of this invention. The cell permits continuous removal of excess ammonia or urea, which is an important form of therapy in an acute or chronic nepatic or kidney failure. In addition, electronic control, and/or combination with implantable batteries or implantble glucose fuel cell (bioautofuel cell) as referred to the Wolfsor, S.K., Jr., Yao, S. J., Geisel, A. and Cash, H. R., Jr., A Single Electrolyte Fuel Cell Utilizing Permselective Membranes, Trans. Amer. Soc. Artificial Internal Organs 16:193–98 (1970) are provided to automatically regulate the rate of blood ammonia, urea, or other toxic substance oxidation of the implanted cell. This hybrid system acts as an artificial metabolic organ to promptly remove the excess ammonia, etc. from a patient without seriously disturbing the body ecology. The same cell may be used in an extracorporeal shunt and, in one embodiment, external DC power is applied for quick removal of excess ammonia, etc. The surgicial implantation and shunt providing techniques are conventional and per se do not form a part of this invention.

Two basic types of cells illustrate the invention, and both involve the use of hydrophobic cathodes. In one alternative, a hydrophilic anode system may be used (FIG. 1) and in a second alternative a hydrophobic anode may be used (FIG. 2). These electrodes are rendered hydrophobic or hydrophilic by controlling the amount of water repellant plastic, e.g. a polyfluorocarbon such as Teflon, in the electrode structure. The hydrophobic cathode has a covering membrane of a silicone rubber, a polycarbonate, a polyfluorocarbon or copolymers thereof which permits diffusion of the oxygen therethrough as the oxidant. The hydrophilic anode employs a membrane thereover of cellulose or a cation exchange resin, and is separated from the hydrophobic cathode by an anion exchange membrane or inorganic matrix. In the case of the hydrophobic anode, a membrane of a silicone rubber, a polycarbonate, a polyfluorocarbon or copolymers thereof for diffusion of ammonia therethrough overlies the hydrophobic anode which is separated from the hydrophobic cathode by an inorganic matrix, the edges of which may be coated with a cation exchange resin to permit diffusion therethrough of ammonium ions.

The entire assembly is adapted for implantation, as by covering the non-membrane surfaces with a silicone or silastic rubber which has proven body-compatible properties. Other encapsulating substances include polyfluorocarbons, polycarbonates or copolymers thereof. The energy produced by the cell is extremely small since the quantities of ammonia are relatively low, from the power point of view, and the energy is dissipated by standard resistors. These resistors are also encapsulated in silicone or silastic, and do not provide sufficient heat that will cause damage to tissues when implanted.

Another aspect of this invention utilizes an electrochemical cell in an extracorporeal shunt system to rapidly oxidize dialysate-ammonia generated by the action of urease on urea in a kidney dialysis unit to harmless, nontoxic nitrogen and water, which are removed by the body by homeostatic processes.

As indicated previously, there have been recent developments in urea removal in hemodialysis that involve the action of urease on urea with the release of large quantities of ammonia as a product. The presence of a high ammonia concentration in the dialysate would rapidly lead to reverse dialysis of ammonia and marked increases in the patient's blood ammonia level. The ammonia can be removed by an electrochemical cell as previously described, while maintaining the advantage that a small volume of water, which is recycled, can replace very large volumes of expensive dialysis fluid. The bulk of equipment is thus also markedly reduced. The ammonia removal system of this invention overcomes the major difficulty of the proposed adsorption or ion exchange systems in that their sorbent-loaded cartridges are eliminated and replaced by the electrochemical cell.

In another embodiment of this invention, an extracorporeal shunt system containing an electrochemical cell with urea selective anodes rapidly and directly oxidizes, electrochemically, the dialysate-urea in hemodialysis to harmless nontoxic products such as carbon dioxide, nitrogen and water which may be reabsorbed by the patient and removed by homeostatic processes. This electrochemical cell is preferably on a closed dialysis loop.

DETAILED DESCRIPTION

Figure 1:
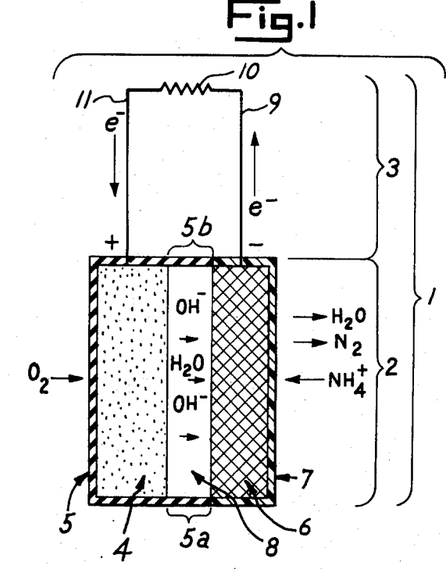
FIG. 1 is a schematic diagram of a cell in accordance with this invention having a hydrophobic cathode and hydrophilic anode.
Figure 2:
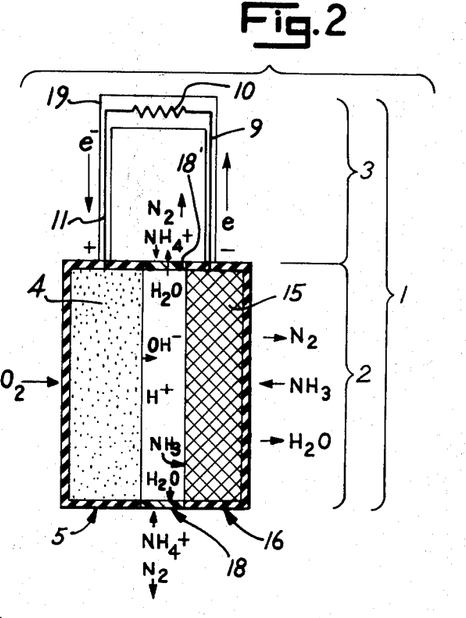
FIG. 2 is a schematic diagram of a cell in accordance with this invention having a hydrophobic cathode and a hydrophobic anode.

FIG. 1 shows schematically, partly in section and partly in plan view, an implantable cell in accordance with this invention having a hydrophobic cathode and hydrophilic anode. The detoxification unit 1 comprises the oxidizing cell portion 2, and the energy dissipating section 3. The hydrophobic oxygen cathode 4 employs hydrophobic catalysts such as hydrophobic silver, silver oxide, gold or other catalysts inert to ammonia. The outer surface of the cathode is coated with a layer of silicone rubber, for example, Medical Type Adhesive silastic by Dow-Corning Company, coating 5 shown in FIG. 1.

The hydrophilic anode 6 is relatively ammonia selective, and typically may be hydrophilic platinum. The anode is coated with a layer or membrane of cationic exchange resin 7. At pH of 7.4, virtually all the ammonia present in body fluids is the form of ammonium ions, $NH_4^+$. The cation exchange layer 7 on the hydrophilic anode 6 allows positively charged ions such as $H^+$ and $NH_4^+$ to pass through, while at the same time not permitting passage or transport of organic substances such as glucose in the body fluids to the anode. With the coatings of silicone and cation exchange membranes over the anodes and cathodes, the cell portion 2 is adapted for implantation in the body.

The cell sandwich 2 also includes an anion exchange membrane 8 as an internal electrolyte in intimate contact with, and sandwiched between, the anode and cathode. Note that the silicone or silastic coating 5 on the cathode 4 covers the edges of the anion exchange membrane 8, as at 5A and 5B. Although the schematic FIG. 1 appears relatively bulky, in actual practice, as seen better from FIGS. 3 and 4, the actual cell portion is wafer-thin. A typical cell has an exposed anode or cathode area on the order of 1 inch in diameter, and may be 3 millimeters thick. An alternative silicone material which may be used is Dow-Corning 3144RTV adhesive/sealant, which is a translucent, room temperature vulcanizing (curing) silicone rubber adhesive, which is noncorrosive to copper.

The opertion of a detoxification cell, e.g. a deammonation cell, implanted in the body, is as follows: Oxygen molecules and water vapor from the body fluids as shown to the left of the cell in FIG. 1 diffuse across the silicone rubber membrane 5 to the hydrophobic cathode 4 where they are reduced to form $OH^-$ ions. The $OH^-$ ions naturally migrate across the anion exchange membrane 8 as shown in this figure to the hydrophilic anode 6. At the same time, ammonium ions from the body fluids diffuse through the cation exchange layer 7 on the anode 6. These $NH_4^+$ ions then are electrochemically oxidized at the interface between the anode and the anion exchange membrane. In the process, electrons are given up to the current collector of the anode and are transported in the external circuit portion 3 of the cell. The reaction products $N_2$ and $H_2O$ diffuse out back through the cation exchange membrane and are removed by the homeostatic processes of the body. It will be noted that this cell simultaneously functions as a water pumping device to keep the cathode dry as well as oxidize the ammonia to nitrogen. This dry cathode system allows the electrochemical cell to operate with effective oxygen mass transfer thereacross.

The electrons released at the anode 6 are transported by a current collector (E.G. gold x-met) internal to the cell 2 and part of the anode assembly 6 to external wire 9. These electrons are transported by the wire 9 to a current consuming device 10, for example, a resistor. The resistor dissipates the energy released from the oxidation of the ammonia at rates and temperatures which do not cause physiological harm to the body. The external circuit is completed by wire 11 passing to the current collector portion of the cathode 4. In an alternative, this external energy dissipating section 3 may also contain, as part of a hybrid unit, a rechargeable storage battery and resistor system connected parallel with the resistor 10. This system permits energy to be stored for monitoring the blood and tissue ammonia level, and to freshen the catalysts of the electrodes and is illustrated in detail in FIGS. 9A and 9B. While the term external has been used, it should be understood to be used in context in connection with the cell, and that the entire deammonation unit 1 is not, in this example, external to the body. Thus, the entire energy dissipating section 3 is conveniently encapsulated with physiologically acceptable materials such as the above mentioned silicones. The anodic, cathodic and overall reactions for ammonia detoxification are illustrated by the equations 1 – 3 below:

$$NH_3(g) + 3OH^- (Soln.) \rightarrow \tfrac{1}{2} N_2(g) + 3H_2O (1.) + 3e^- \quad E°_{298} = -0.77 \text{ v (Anodic Reaction)} \quad \text{(Eq. 1)}$$

$$O_2(g) + 2H_2O(1.) + 4e \rightarrow 4OH^- (Soln.) \quad E°_{298} = 0.40 \text{ v (Cathodic Reaction)} \quad \text{(Eq. 2)}$$

$$4NH_3(g) + 3 O_2(g) \rightarrow 2N_2(g) + 6H_2O (1.) \quad E°_{298} = 1.17 \text{ v (Overall Reaction)} \quad \text{(Eq. 3)}$$

FIG. 2 is a diagram, in part in schematic, for a second embodiment of the invention which employs a hydrophobic anode. The cathode of the invention is as above described. However, the anode 15 is a hydrophobic catalyst-containing anode which is covered with a gas permeable membrane or layer 16 (e.g., silicone rubber), which is permeable to gaseous ammonia dissolved in the body fluids. The oxygen is also dissolved in the body fluids and both are supplied to the cathode and anode respectively, in the gaseous state. The cell sandwich also contains an inorganic matrix solid electrolyte separator 17 between the hydrophobic cathodes and anodes. The outer surface of both the anodes and cathodes are coated with a thin layer of silicone rubber, 5 and 16, respectively. The edges of the inorganic matrix separator 17 are coated with cation exchange resin 18, 18'. The $NH_4^+$ ions from the body fluids are transported across the cation exchanger resin 18, 18', at the edge of the central inorganic matrix separator which acts as a solid, yet permeable electrolyte. Within the separator 17, the equilibrium $NH_4^+ = NH_3 + H^+$, favors the formation of $NH_3$, since $H^+$ combines with $OH^+$ ions produced at the cathode to form water molecules. The separator 17 thus also serves as an $NH_3$ gas generator. Accumulated water molecules diffuse across the cation exchange resin 18, 18' to the exterior of the unit. This outward flow of water from the separator to the body fluids provides a low viscosity environment around the entire unit which enhances the mass transfer of $NH_4^+$ ions, $O_2$ and $N_2$ molecules.

The $OH^+$ ions which are needed for the anodic oxidation of $NH_3$ and for maintaining a high pH in the separator are produced from the cathodic reduction of $O_2$. The anodic, cathodic and overall reactions are as above shown in equations 1 – 3. The electrons produced by the anodic reaction are passed as before to the external energy dissipating portion of the cell 3 via wire 9 and resistor 10. The external circuit is completed and provides electrons for the cathodic reaction, Equation 2, above, via wire 11. As described above, a silicone coating 19 may be used to encapsulate the wires and resistor external to the oxidizing cell portion of the deammonation unit 1.

The electrochemical cell portions 2 of the entire deammonation unit 1 as above described in connection with FIGS. 1 and 2 may be arranged in parallel into a multicell assembly which is then hybridized by connection to a rechargeable storage battery and a potentiostat. See for example, FIGS. 9A and 9B. The storage battery per se is relatively conventional, and per se does not form part of this invention. Typically, it may be nickel cadmium cells of appropriate capacity, such as in a battery which will store a high percentage of its full charge at a potential of approximately 0.4 volts. When the deammonation unit is operating at a peak rate of ammonia removal, the electricity generated by the oxidation of the ammonia is stored in the battery. When there is a low ammonia concentration, electricity from the storage battery is fed back to the cell assembly by virtue of reversing polarity of the battery connection to maintain a constant potential and constant rate of ammonia removal. Provision for measurement, and/or recording the magnitude and direction of the current in the feed-back system provides a monitor of blood or tissue ammonia level. An alternative to the Ni–Cd or other storage battery is the case where a (glucose) bioautofuel cell is implanted as part of the system to produce a driving current source by oxidation of glucose in body fluid. This bioautofuel cell per se is not part of this invention and is described above in the Wolfson et al article 16 TASAIO 193-198.

As noted above, this cell is particularly adaptable for implantation within the body. However, the units may be employed as a device for fast blood-ammonia removal in conjunction with a hemodialyzer of conventional construction, which, per se, does not form a part of this invention. The ammonia selective anodes as above described may be connected to various types of cathodes which may utilize the oxygen from the blood directly, or may be provided with an external air or oxygen supply. An external direct current is applied to the cell to speed up the electrochemical oxidation of the blood ammonia to nitrogen and water at the anode. The use of such DC power supply provides a means of fast ammonia removal for cases of severe hepatic failure.

ADDITIONAL EMBODIMENTS

Figures 3, 4, 5:
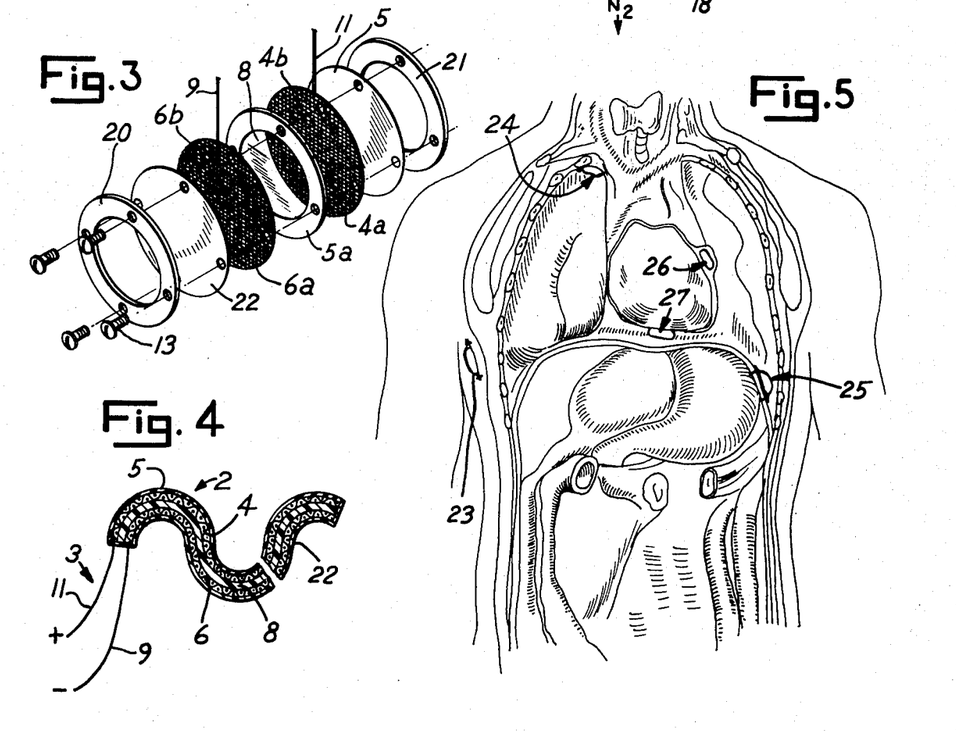
FIG. 3 is an exploded view showing the component parts of a typical cell of this invention.
FIG. 4 is a section view through a typical cell such as in FIG. 3 showing the flexibility of such cells and a corrugated construction to increase surface area.
FIG. 5 shows typical thoracic cavity or subcutaneous locations for implantation of cells in accordance with this invention.

FIG. 4 illustrates in section view a cell of this invention in a folded configuration to increase the surface area of the cell. Anion exchange membrane 8 is sandwiched between a pair of catalyst-filled X-Met or screen current collectors with the catalyst side facing the membrane 8. The current collector with catalyst forms the anode and cathode assemblies 6 and 4 respectively. The cathode assembly 4 is overcoated or covered with a silicone rubber membrane and the anode assembly 6 with a cellulose membrane 22. This cell may be used implanted or extracorporeal. For example, the cell may be connected to an arteriovenous shunt in the radial artery such as is used in hemodialysis. In the alternative, the cell may be implanted in the peritoneal cavity and connected to the internal iliac artery and vein.

Figure 6:
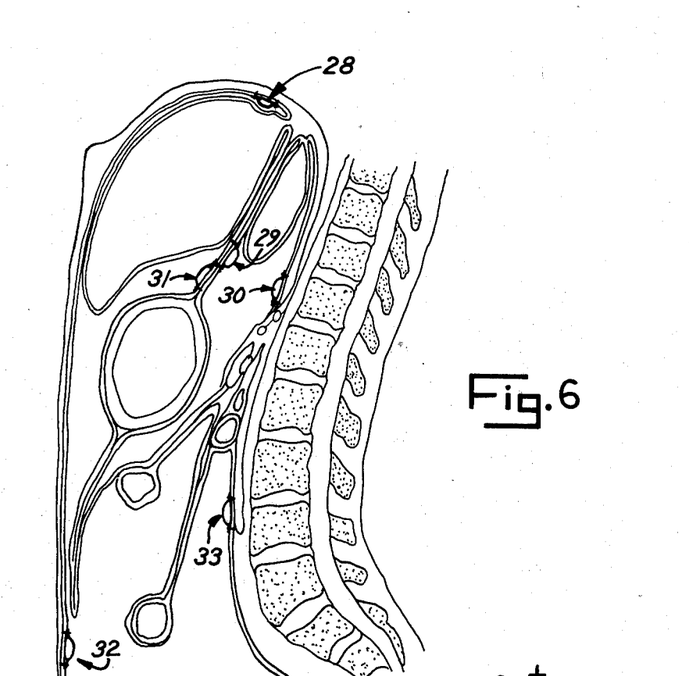
FIG. 6 shows typical locations for implantations of cells in accordance with this invention within the abdominal cavity.

FIGS. 5 and 6 illustrate typical implantation sites, with FIG. 5 showing thoracid cavity or subcutaneous sites, and FIG. 6 showing typical abdominal cavity sites. A unit 1 may be placed in the subcutaneous fat pad 23 in a manner similar to a cardiac pacemaker implant. Other locations involve placement (by suturing a flap of silicone rubber molded on the unit 1) intrapleurally, e.g., in the apex of the pleural cavity 24 or in the costophrenic angle 25, intrapericardially, e.g., in the pleural pericardium 26 or the diaphragmatic pericardium 27. The cells may be preshaped to conform to the receiving cavity or site, as above noted in FIG. 4.

FIG. 6 illustrates typical locations for the units within the abdominal cavity, for example, subdiaphragmatic attachment to the diaphragm near the coronary ligament 28. In the lesser sac, the units may be sutured into place on the lesser omentum 29, or the posterior abdominal wall 30. In the greater sac, the unit may be placed on the lesser omentum at 31, on the anterior abdominal wall at 32 or the posterior wall at 33.

Figure 7:
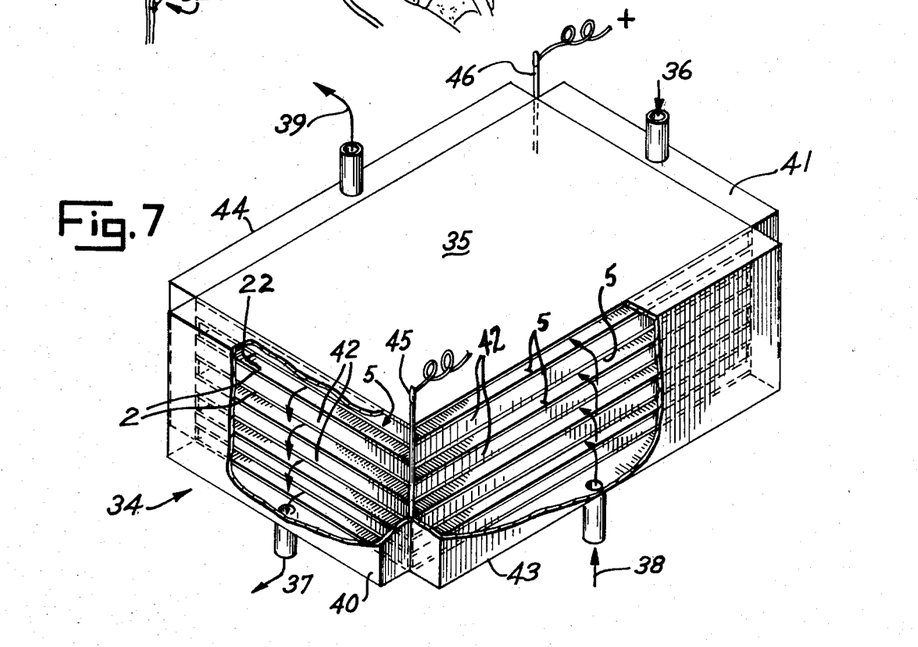
FIG. 7 shows in schematic perspective the extracorporeal shunt system employing a series of cells in accordance with this invention.
Figure 8:
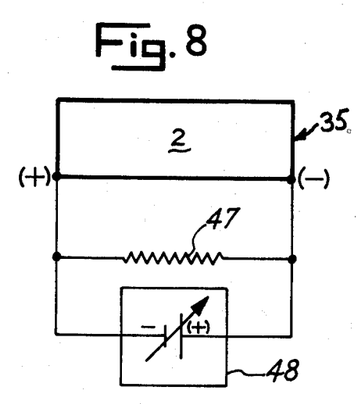
FIG. 8 is a schematic electrical diagram of the extracorporeal shunt system of this invention showing the power supply and resistors.

FIG. 7 illustrates units assembled in an extracorporeal shunt unit 34. Housing 35 has provision for blood inlet 36 and blood outlet 37, air or $O_2$ inlet 38 and exhaust air $O_2$ outlet 39. Manifolds 40 and 41 serve to distribute and collect, respectively, the blood to the anode side 22 of the cell portions 2. Baffles 42 close off the edges of the blood and oxygen spaces on alternate sides. The cells are oriented with like faces facing each other and thus alternate with respect to top and bottom of unit. Manifolds 43 and 44 likewise distribute and collect, respectively, air or $O_2$ to the cathode side 5 of the cell portions 2. Bus bars 45 and 46 are connected respectively to the current collectors of the anode and cathode current collectors, respectively (not shown) and wires 9 and 11 are connected across a DC power source, such as a battery, to provide energy for rapid oxidation of the toxic substance such as ammonia. This electrical schematic is illustrated in FIG. 8 in which cell 2 is connected in parallel across resistor 47 and variable external power source 48.

Figure 9A:
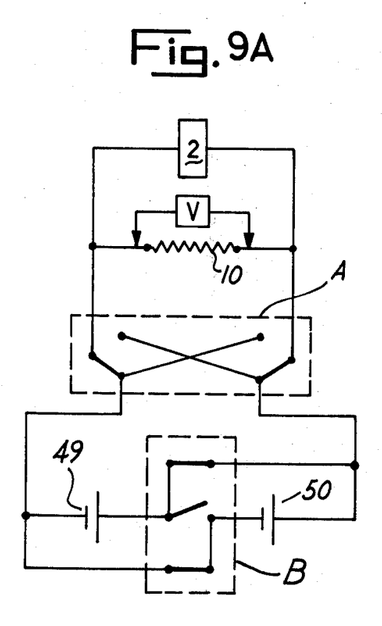
FIGS. 9A and 9B illustrate the electrical schematic of the hybrid system in two modes of operation, that of high toxic substance concentration (FIG. 9A) and that of low toxic substance concentration (FIG. 9B).
Figure 9B:
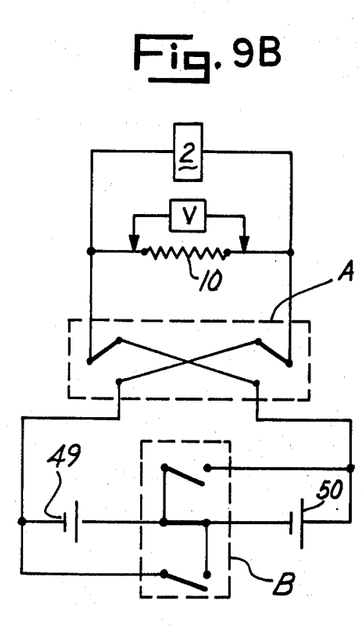

FIGS. 9A and 9B show two modes of a hybrid system embodiment of this invention for completely implanted units. Cell 2 is connected in parallel with resistor 10, and to batteries 49 and 50 as above described. Switch units A and B are pottable solid state switching circuits, here represented for simplicity as ganged switches. Switch A reverses polarity and switch B changes the connections from series to parallel and vice versa. The change of state of these switch units from the mode shown in FIG. 9A to that in FIG. 9B is dependent on the potential difference across the cell 2 and resistor 10 as shown by the reference V. The mode of FIG. 9A illustrates the circuitry setting for a condition of high ammonia concentration with the secondary cells 49 and 50 being charged by the cell 2 in a parallel configuration due to the high rate of ammonia oxidation. As the voltage V, across the cell 2 drops, the state of the switches is triggered to that of the mode shown in FIG. 9B. In this mode the secondary cells 49 and 50 discharge in series through the cell 2 to increase the current, driving the cell 2 to increase ammonia oxidation. By the addition of two more switches in switch circuit B for each additional secondary battery cell, the number of secondary cells can be increased to achieve the desired drive voltage.

Figure 10:
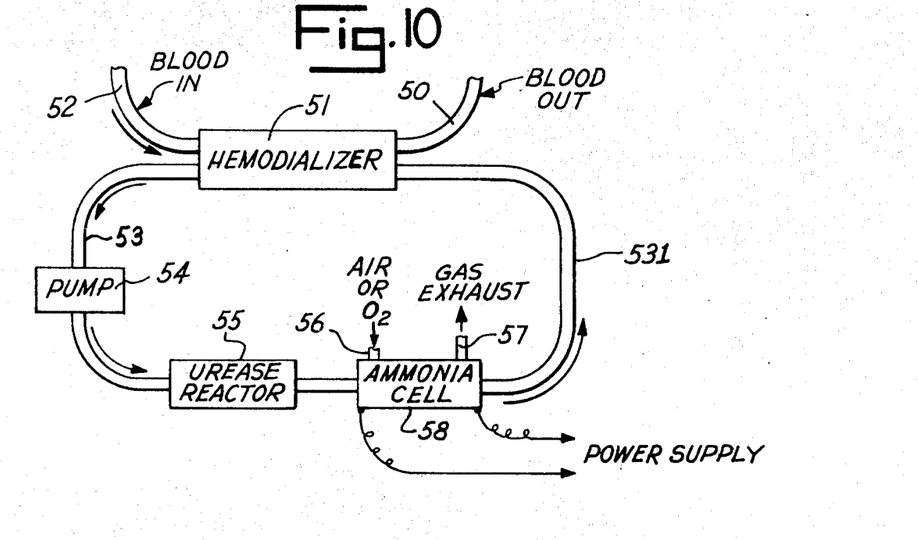
FIG. 10 illustrates, schematically, an embodiment of this invention wherein an electrochemical cell assembly is connected to a urease-loaded cartridge, with the dialysate flowing first through the urease cartridge before it reaches the electrochemical cell assembly.
Figure 11:
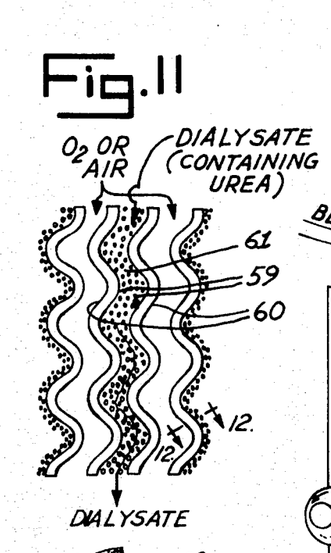
FIG. 11 is a schematic diagram illustrating the interior of an electrochemical cell assembly wherein the anode surfaces are exposed to urease-loaded microcapsules.
Figure 12:
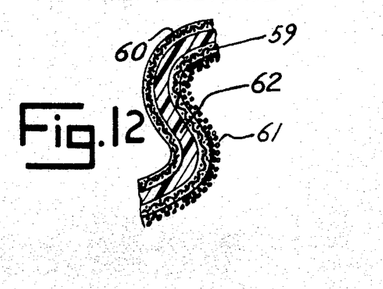
FIG. 12 is a detailed, sectional view of a urease-loaded electrochemical cell taken along section line 12—12 of FIG. 11.

In FIGS. 10, 11 and 12, the above-described electrochemical cells may be employed in any conventional extracorporeal shunt system as a device for fast dialysate-ammonia removal. The ammonia selective anodes in the cell are as described previously and may be connected to various types of cathodes which utilize oxygen directly from the dialysate, or the cells may be provided with an external air or oxygen supply 56 as illustrated in FIG. 10. The cell units may also be filled with urease-loaded microcapsules as illustrated in FIG. 11 instead of being connected to a separate upstream urease-loaded cartridge 55 as shown in FIG. 10. After flowing through either system illustrated in FIGS. 10 and 11, the deammonated dialysate 531 will be recirculated for repeated removal of uremia waste metabolites. An external direct current may be applied to the cell units to accelerate the electrochemical oxidation of the dialysate ammonia to nitrogen and water at the anode.

More particularly, referring to FIG. 10, blood from a patient is passed into a conventional hemodialyzer 51 by conventional conduits 50 and 52 wherein blood waste products are removed by a constantly circulating dialysate flowing in closed loop 53 through the pumping action of pump 54. The dialysate, as it leaves the hemodialyzer 51, is first contacted with urease capsules contained in urease reactor 55 to convert urea to ammonia. The dialysate containing ammonia is then passed to ammonia cell 58, similar in construction to the cell illustrated in FIG. 7 and connected to a suitable DC power source wherein the ammonia is oxidized by gaseous $O_2$ (i.e. air) entering inlet 56. Unused oxidant and inerts are continuously expelled through exhaust conduit 57. The ammonia is oxidized in cell 58 to nontoxic nitrogen and water which are ultimately expelled by the body by normal homeostatic processes.

In a preferred embodiment illustrated in FIGS. 11 and 12, the function of urease reactor 55 is incorporated directly into cell 58. Cell 58 is similar in construction to the cell illustrated in FIG. 4 except that urease capsules 61 are packed between convoluted individual alternating cells defined by anode 59 and cathode 60. In each individual cell, the cathode 60 and anode 59 are separated by a suitable anion exchange membrane 62.

As mentioned previously, the electrochemical cells may be employed in an extracorporeal shunt system as a device for fast dialysate-urea removal. The urea-selective anodes may be connected to various types of cathodes which utilize oxygen from the dialysate directly, or from an external air or oxygen supply. After passing through a hemodialyzer and the electro-chemical deureator, the deureated dialysate is then recirculated to the hemodialyzer for repeated removal of uremia waste metabolites. An external DC currnet may be applied to the cell units to speed up the electrochemical oxidation of the dialysateurea to nontoxic products shch as carbon dioxide, nitrogen and water at the anode. As a result, the whole dialysis system is made portable.

Figure 14:
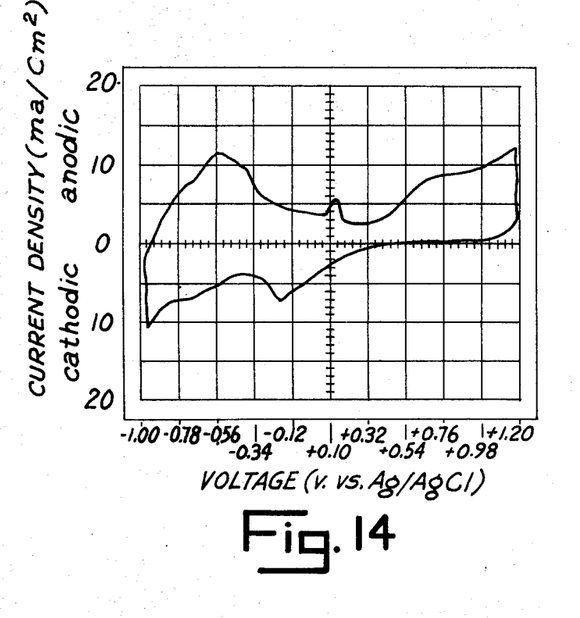
FIG. 14 illustrates an oscilloscope (cyclic) scan that is obtained as urea is oxidized in a phosphate buffer solution in accordance with this invention.

In more detail, the direct removal of urea from dialysate is schematically illustrated in FIG. 14 wherein blood flows through hemodialyzer 51 through conduits 50 and 52 to selectively transfer urea and other impurities to the dialysate flowing in closed dialysate loop 53.

In the cell 70 in this loop, the dialysate contacts an anode 73 (which for example, may be of similar construction to that structure illustrated in FIG. 7). Cathode 74 is contacted with air flowing into cell 70 through conduit 71 and exiting through conduit 72. As a result, the urea is converted to harmless $CO_2$, $N_2$ and water. The conversion rate of urea by anode 73 can be increased by driving the cell through DC power supply 76 which is connected to cell 70 by leads 75, 75′.

EXAMPLE I

The following example has reference to FIG. 3 which shows in exploded perspective an electrochemical cell in accordance with this invention having an anode and cathode of 1 square centimeter area. The unit as shown is of the type illustrated specifically in FIG. 1. Clamped between rings 20 and 21 by means of screws 13 are the following parts reading from left to right: The cellulose membrane 22 lies over the anode assembly 6 which comprises a gold X-Met current collector 6A into which is impregnated platinum and Teflon powder 6B as the anode catalyst material. The external wire circuit 9 is connected to the gold current collector 6A. The anode assembly is in contact with a quaternary ammonium anion exchange membrane 8 which is contained within a silicone gasket rim 5A. This in turn lies against the cathode assembly 4 which comprises a silver X-Met screen current collector 4A into which is impregnated a silver and Teflon powder 4B. The external circuit wire 11 is attached to the silver screen. A silicone rubber membrane 5 is placed over the exterior surface of the cathode assembly 4. The right-hand ring 21 completes the assembly which is screwed together to insure good contact of the parts. The edges of the assembly and the external wires may be then painted with a silicone (medidal type A) adhesive or the Dow-Corning 3144RTV adhesive/sealant.

The cell was immersed in a Krebs-Ringer bicarbonate buffer solution of pH 7.4. The oxygen concentration in the buffer was the same as physiological, that is, 85 Torr. Ammonium chloride at a concentration of 60$\mu$M provides an $NH_4^+$ concentration of about 1 $\mu$g/ml. Under these conditions, the cell exhibited an open circuit potential of 0.40 volts at room temperature. In operation, the cell exhibited a potential of 0.22 volts at a constant current density of 22 $\mu$A/cm$^2$.

With these operating properties, a deammonation unit having an electrode surface area of 20 cm$^2$ operating at 1 mA/cm$^2$ would clear up a total of 20 mg. ammonia in about 4 hours. The arterial ammonia level of a patient would fall from 4 $\mu$g/ml in such a 4 hour run to about 2 $\mu$g/ml. In an approximate run of another 1 – 2 hours, the normal blood level of about 1 $\mu$g/ml would be achieved.

EXAMPLE II

Figure 13:
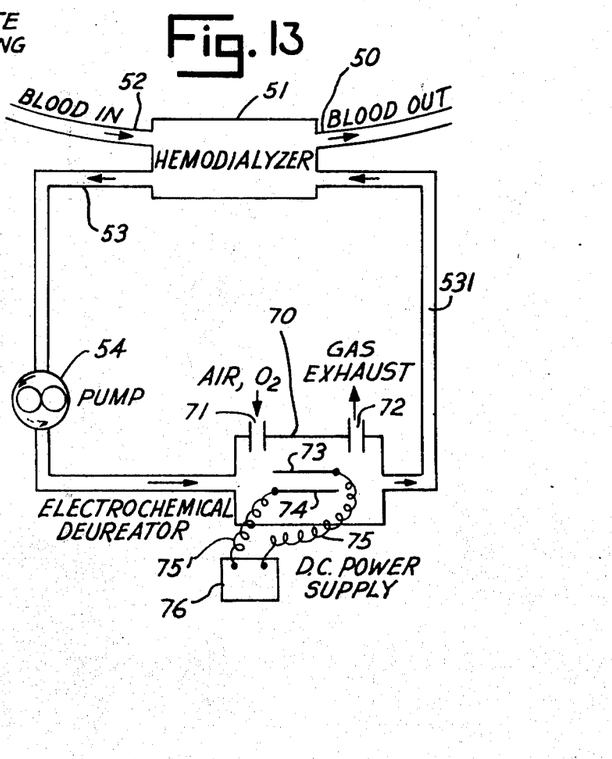
FIG. 13 is a schematic diagram of an extracorporeal shunt deureator system wherein a urea selective anode converts urea directly to harmless products.

The following example has reference to FIG. 13 wherein urea is directly oxidized electrochemically without prior enzymatic hydrolysis with end products being $N_2$, $CO_2$ and $H_2O$. The experiments performed involved: linear potential scans of ammonium chloride, urea, and glucose plus urea, in phosphate buffer solutions, and anodic oxidation of glucoseurea in bicarbonate buffer in extracorporeal electrochemical cells.

An Electrochemistry System Model 170 scanner (Princeton Applied Research Corp.) was used for the linear potential scanning studies. The system is similar to the one employed in previous studies on anomeric effects in the electrodic oxidation of carbohydrates. (Yao, S. J., Appleby, A. J. and Wolfson, S. K., Jr., Zeitschrift für Physikalische Chemie, (Neue Folge) 82; 225–235, 1972) The working electrode (i.e., electrode being evaluated) was a disc of 1 cm$^2$ smooth platinum. Ag/AgCl was used as the reference electrode of known potential. The counter-electrode was a 4 cm$^2$ platinum black (40 mg Pt/cm$^2$). The electrolyte was Krebs-Ringer phosphate buffer at pH 7.4. Triangular potential sweeps were conducted over a range of −1.00 v to +1.00 v vs. Ag/AgCl, i.e., −0.32 v to +1.68 v vs. RHE (Reversible Hydrogen Electrode potential at the pH of the solution), at a scan rate of 0.20 v/sec. Potential/current curves were recorded on either an oscilloscope or an x-y recorder. The potential sequence used to achieve a well-defined Pt surface followed from that of Giner and Malachesky. (Giner, J. and Malachesky, P., Proc. Artif. Heart Program Conf., U.S. Dept. Health, Education and Welfare, 1969, pp. 839–848) The general character of the scan also closely resembles similar plots obtained in phosphate buffer by Giner and Malachesky. FIG. 14 shows the cyclic scan recorded for 2.0 M urea in a phosphate buffer. A time-invariant oxidation peak appears at around 0.12 v vs. Ag/AgCl (i.e., round 0.80 v vs. RHE) in the anodic scans of the urea solution. The same peak appears in the glucose plus area solution (0.80 M glucose and 2.0 M urea) but is not seen in the scans of both solutions of buffer alone and of $NH_4Cl$. The chemisorbed species at 0.80 v vs. RHE is believed to be reduced $CO_2$ as produced by the urea adsorption. As a result, the urea of directly oxidized at a Pt anode with the products of the oxidation being $CO_2$, $N_2$ and $H_2O$. $NH_4^+$, $NO_3^-$ and $NO_2^-$ were not found to be products of the anodic reaction.

EXAMPLE III

Experiments on deureation by anodic oxidation were carried out in extracorporeal electrochemical cells. This cell was made of a sandwich of electrodes and permselective membranes and assembled in a flow-thru system similar to FIG. 7. The sandwich consisted of a hydrophilic Pt -black anode, an anion exchange membrane and a hydrophobic Pt- black cathode.

The anion exchange member was an AMFion A-100 membrane manufactured by American Machine and Foundry Co., Stamford, Connecticut. This membrane has a polyethylene backbone containing polyelectrolytes of quaternized ammonium thereby rendering the membrane permeable to negative (anion) groups.

The Pt-black anode was manufactured from a paste of porous platinum black having a surface area of 25 M$^2$/g in 25% polytetrafluoroethylene (Teflon) by pressing the paste, without sintering, to 200 psig over a gold X-Met current collector. The resultant anode had a thickness of 25 mils and contained 15 g/ft$^2$ of Pt black.

The cathode was manufactured from a paste of porous platinum black (25 M$^2$/g) and 25% Teflon by pressing the paste, with sintering to cure the Teflon, at 2000 psig over a gold X-Met. The resultant cathode contained 15 g/ft$^2$ of Pt black and was painted with silicone so that it would be porous to gas only.

Figure 15:
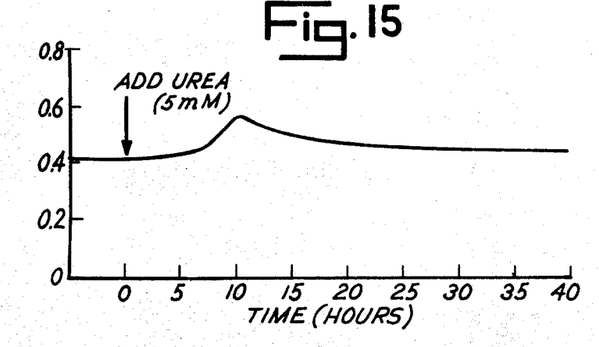
FIG. 15 illustrates the effect of adding urea to an electrochemical cell operating with glucose in a bicarbonate buffer at the anode and air at the cathode.

The anode was covered with a cellulose membrane and was exposed to a flowing glucose-urea solution or plasma-dialysate (Po$_2$ of 85 mm Hg, Pco$_2$ of 36 mm Hg and at pH 7.4). The cathode was in direct contact with flowing air. Current flow was produced either by shunting the cell with a resistor or by the application of an external power source (D.C.). FIG. 15 shows the effect of added urea (5 mM) on an electrochemical cell operating with 5 mM glucose in bicarbonate buffer at the Pt anode, flowing air at the Pt cathode and under 5 k ohm passive load. The cell voltage went up from 0.41 v to a maximum at 0.57 v within 12 hours following addition of the urea to the glucose solution. Similar voltage enhancement by the effect of addition of plasma or its dialysate, both containing urea, to an operating implantable glucose fuel cell consisting of a Pt anode and an Ag cathode was also observed.

The above example shows that urea can be anodically oxidized to end products such as $CO_2$. $N_2$ and $H_2O$ by an extracorporeal electrochemical deureator which utilizes Pt-black or other catalysts, electricity and air. This approach eliminates the step of action of urease on urea and the need for an expensive adsorbent such as zirconium phosphate to remove the $NH_4^+$ thus formed. As a result, the entire renal dialysis system may be made portable.

EXAMPLE IV

The role of elevated levels of normal blood and tissue components upon the function of an implantable glucose fuel cell (bioautofuel cell) is demonstrated in this example. Components studied included urea, creatinine, alanine, ammonia and a frequently ingested abnormal substance, ethanol. The effect of these specific substances and/or plasma, plasma dialysate and plasma residual after dialysis on an operating glucose fuel cell was determined.

Briefly, most of these substances inhibited the performance of fuel cells containing platinum catalysts exclusively. However, the use of an $O_2$-specific cathode (Ag) prevents such inhibition.

Initially, plasma, plasma dialysate and the plasma macromolecule residual after dialysis (mostly proteins and glycoproteins) are separately added to an in vitro glucose fuel cell operating under controlled conditions and having the anode covered with a membrane, i.e., cellulose film similar to a dialysis membrane. Thereafter, the effects of several specific normal constituents of plasma ultrafiltrate on the cell was determined when added individually to the glucose fuel cell. Also, several "abnormal" substances were similarly studied. These substances were ones (such as ethanol and ammonia) which can be present in body fluids under certain circumstances such as after imbibing alcoholic beverages and in disease states such as acute or chronic hepatic failure (hepatitis or cirrhosis).

Two types of in vitro fuel cell systems were employed. The first type of cell was composed of separate half-cells where electrodes consisting of suitable catalysts were immersed in beakers containing a simulated body electrolyte (Krebs-Ringer-bicarbonate). In this half-cell system, the half-cells were connected by agar-agar saturated KCl bridges. The anode was provided with glucose in a physiological concentration (5 mM) and equilibrated with a mixture of 5% $CO_2$ and balance $N_2$ (pH 7.4, $P_{CO_2}$ 35–40 torr, $P_{O_2}$ < 5 torr). The cathode was immersed in a similar fluid equilibrated with a mixture of 5% $CO_2$, 12% $O_2$ and balance $N_2$ (pH 7.4, $P_{CO_2}$ 35–40 torr, $P_{O_2}$ 85 torr). When the cell charged to a standard operating level of about 50 micro-amps/cm² through a 5–10 K ohm load, the test substance was added to the anode or cathode half-cell.

The second system employed an implantable sandwich cell with anode and cathode compressed in a wafer configuration with an anion exchange membrane between as illustrated in FIG. 3. The cell was immersed in a single beaker containing Krebs-Ringer-bicarbonate electrolyte and equilibrated with gas as above (pH 7.4, $P_{CO_2}$ 35–40 torr, $P_{O_2}$ 85 torr). In this cell the anode was covered by a cellulose film (Nephrophane, a sodium-cellulose-xanthogenate membrane manufactured by Filmfabrik Wolfen, East Germany) and the cathode by 10 mil silicone rubber, medical grade, adhesive film (Silastic, Cat. No. 500-36 HH 0806 as manufactured by Dow-Corning). The cathode operates dry by virtue of the fact that the covering membrane admits only gas vapors, and the anion exchange membrane electrolyte conducts $OH^-$ (produced by reduction of $O_2$) away from the cathode to the anode where product water is formed by combination with protons liberated by oxidation of fuel (glucose). In this case, test substances were added to the electrolyte and had simultaneous access to both anode and cathode covering membranes.

The test substances were of two kinds. The first is a number of individual specific compounds as described in detail below. The second is whole plasma, and plasma products obtained by dialysis. For this purpose, whole human plasma was obtained from a blood center. The blood had been collected in a bag containing 67.5 ml ACD anticoagulant solution (0.8% citric acid, 2.2% sodium citrate and 2.45% glucose). This resulted in a glucose concentration of 455 mg % in the plasma after separation. A portion of the plasma was dialyzed overnight at 4° C vs the same buffer used in the tests with individual substances. The dialysis was carried out by placing 100 ml plasma in a cellulose dialysis sac (AHT Co., 1 inch dialysis tubing 0.0008 thick) which should retain substances of MW > 12,000. This tubing was thoroughly washed with water to remove all traces of glycerol before use. The dialysate was then further diluted with an equal volume of buffer before being placed in the test cell. Concentrations of its various components are listed in Table 1.

TABLE 1

| | Composition of Fluids Used for Plasma Studies of Example 4 | | | | | |
|---|---|---|---|---|---|---|
| | Starting Material | | | Final Concentration in Cell | | |
| | Whole Plasma | Plasma Dialysate | Macro-molecular Residual | Exp. I | Exp. II | Exp. III |
| Protein (gm %) | 6.4 | 0* | 5.6 | 1.2 | 0 | 1.2 |
| Glucose (mg %) | 455 | 157 | 0* | 153 | 154 | 153 |
| Urea (mg %) | 22 | 8 | 0 | 4 | 4 | 0 |
| Creatinine (mg %) | 1.0 | 0.3 | 0* | 0.2 | 0.2 | 0 |
| Uric Acid (mg %) | 3.7 | 1.1 | 0* | 0.7 | 0.6 | 0 |
| Chloride (mEq/1) | 73 | 109 | 117 | 118 | 119 | 126 |
| Sodium (mEq/1) | >160 | 152 | 150 | >149 | 149 | 147 |
| Potassium (mEq/1) | 3.9 | 5.0 | 6.6 | 8.3 | 6.7 | 7.7 |
| Phosphate (mEq/1) | 3.2 | 3.7 | 3.6 | 3.5 | 3.7 | 3.6 |
| Calcium (mg %) | 9.2 | 2.9 | 0* | 1.7 | 1.5 | 0 |
| Alk. Phase (Units) | 100 | 0* | 94 | 19 | 0 | 20 |
| Cholesterol (mg %) | 145 | 0* | 130 | 27 | 0 | 27 |

*These values were less than the lower limit of detection on the autoanalyzer and are presumed to be essentially zero.

\* These values were less than the lower limit of detection on the autoanalyzer and are presumed to be essentially zero.

We then tested whole plasma diluted in a manner so that the dialyzable components of the plasma were present in the same concentration as they were in the dialysate-only test. This renders differences in the results dependent only upon the presence or absence of plasma macromolecules. This was accomplished by using a final dilution of plasma which provided the same concentration of glucose, urea, etc. as in the dialysate test. The third experiment in this series involved the addition of only the plasma protein. To this end the dialysis of the plasma was continued after removal of the original dialysate. The buffer was changed 5 times over a period of 72 hours to remove remaining amounts of dialyzable substances. We adjusted the plasma protein concentration to that of the whole plasma experiment to render all the tests comparable. Thus, the concentration of substances common to more than one of the experiments was always approximately equal. Glucose was added, as needed, to keep its concentration at 8.5 mM (154 mg %) in all 6 cells.

The substances investigated in the 5 mN glucose cell were creatinine, alanine, ethanol, ammonium chloride, urea, diluted whole plasma, plasma dialysate and macromolecule residual.

The agar-agar KCl bridge type cells were used to determine the individual effects on either the anode or the cathode of an operating glucose fuel cell (10 K ohm load). Either hydrophobic silver (Ag) or hydrophobic platinum (Pt) was used as the cathode while hydrophilic platinum was used as the anode in all cases. Normal and abnormal amounts of various test substances were separately added to either the anode, the cathode or both half-cells at room temperature. The results of voltage change during a 6-hour run under 10 K ohm load following this addition are compiled in Table 2.

the substances tested exhibited a poisoning effect on the cells. Creatinine poisoned the anode at the abnormal concentration. It was observed that all Pt/Pt (anode/cathode) cells experienced poisoning when abnormal concentrations of the above substances were present at both anode and cathode. In general, no poisoning was observed when the cells were made of Pt anode and Ag cathode.

Figure 16:
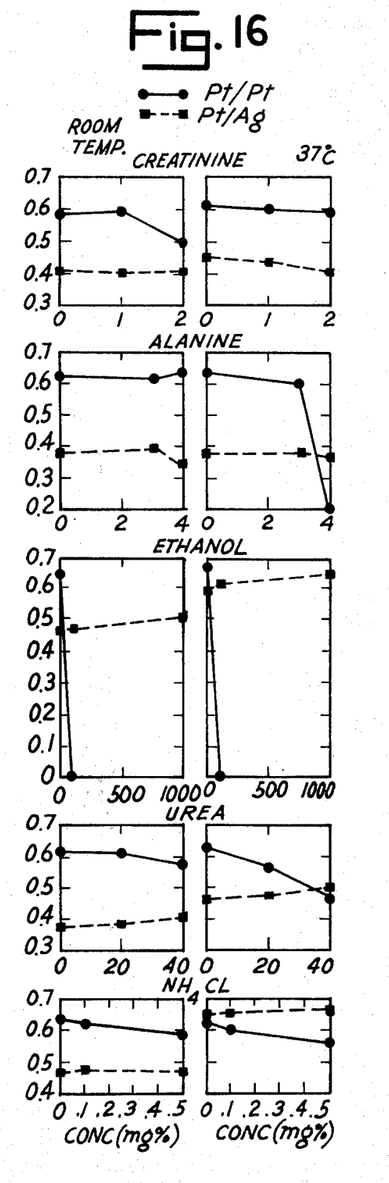
FIG. 16 illustrates the effect of adding endogenous substances to sandwich cells of the general type illustrated in FIG. 3.

Effects of added endogenous substances on Pt/Pt and Pt/Ag sandwich cells at room temperature and at 37° C are illustrated in FIG. 16. NOne of the substances caused appreciable poisoning of the Pt/Ag sandwich cells. Urea and ethanol seemed to enhance the performance of these operating cells at higher concentrations. The voltage values demonstrate that ethanol, urea and ammonia can be oxidized, and the body thereby detoxified of such substances. Conversely, all Pt/Pt sandwich cells were poisoned to various degrees by these added substances and show specificity of the Pt/Ag cells of this invention. These results are consistent with those of the salt-bridge type fuel cells and clearly indicate that poisoning is occurring at the Pt-cathode where adsorption and oxidation of the added substance take place.

We believe that the presence of these substances at the Pt-cathode results in anode type reactions, thus causing a reduction of voltage under loading condi- Table 2

Separate Additions of Substances to Salt-Bridge Type Anode and/or Cathode Half-Cells (Room Temperature) *

| | Pt/Pt | | | Pt/Ag | | |
|---|---|---|---|---|---|---|
| | Anode mg % | Cathode mg % | Voltage (v) | Anode mg % | Cathode mg % | Voltage (v) |
| Creatinine | 0 | 0 | 0.60 | 0 | 0 | 0.33 |
| | 1 | 0 | 0.60 | 1 | 0 | 0.33 |
| | 2 | 0 | 0.50 | 2 | 0 | 0.33 |
| | — | — | — | 2 | 1 | 0.33 |
| | 2 | 2 | 0.43 | 2 | 2 | 0.30 |
| Alanine | 0 | 0 | 0.54 | 0 | 0 | 0.40 |
| | 3 | 0 | 0.54 | 3 | 0 | 0.40 |
| | 4 | 0 | 0.52 | 4 | 0 | 0.31 |
| | — | — | — | 4 | 3 | 0.38 |
| | 4 | 4 | 0.50 | 4 | 4 | 0.36 |
| Ethanol | 0 | 0 | 0.66 | — | — | — |
| | 100 | 0 | 0.67 | 1000 | 0 | 0.43 |
| | 1000 | 0 | 0.68 | 1000 | 100 | 0.39 |
| | 1000 | 100 | 0 | 1000 | 1000 | 0.42 |
| Urea | 0 | 0 | 0.60 | 0 | 0 | 0.42 |
| | 20 | 0 | 0.60 | 20 | 0 | 0.42 |
| | 40 | 0 | 0.58 | 40 | 0 | 0.42 |
| | — | — | — | 40 | 20 | 0.42 |
| | 40 | 40 | 0.54 | 40 | 40 | 0.41 |
| Ammonium Chloride | 0 | 0 | 0.58 | 0 | 0 | 0.40 |
| | 0.5 | 0 | 0.58 | 0.5 | 0 | 0.40 |
| | 2.5 | 0 | 0.56 | 2.5 | 0 | 0.40 |
| | — | — | — | 2.5 | 0.5 | 0.40 |
| | 2.5 | 2.5 | 0.53 | 2.5 | 2.5 | 0.38 |

* Low values were chosen to be in the normal range of human blood. High values were those which might be present in abnormal states. (Ethanol values imply "social" and excessive drinking.) Logistics were such that the data for empty spaces were not obtainable in the same electrolyte and fuel mixture. Since the substitution of Ag for Pt in the cathode implies no change in anode performance, it is possible to evaluate the effect of substances added to the cathode alone without repeating the zero and low concentration of the substance in the anode.

It was shown that within the first 6 hours, there was no appreciable bacterial growth or diffusion of added substances across the salt bridge; therefore, the six-hour time interval was chosen as a standard testing period. At the normal level of concentration, none of tions. The added substances did not affect the salt-bridge itself or the anion exchange membrane since both salt-bridge and sandwich types of Pt/Ag cells were not poisoned.

Further, our experimental results show no appreciable Cl⁻ poisoning as suggested by other researchers. The prevention of such poisoning at the Ag cathode is attributed to the dry-cathode design of the fuel cell of this invention. The rationale of this particular design is that the anion exchange membrane (AIEM) does not just serve as an internal electrolyte or separator. It is also a component of a pumping mechanism to drive the OH⁻ ions (produced from the cathodic reduction of $O_2$) or, indirectly, drive the $H_2O$ from the cathode to the anode. Thus, with the exception of the immediate cathode/AIEM interface, the cathode can be maintained dry. Furthermore, at the interface, the high concentration of OH⁻ ions present there could prevent the formation of AgCl. Therefore, it is believed that the Cl⁻ ions do not actually reach the Ag catalyst and thus no Cl⁻ poisoning can occur.

Figure 17:
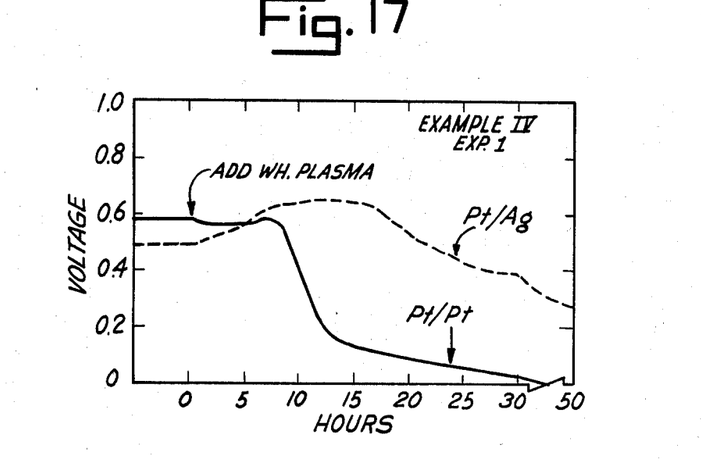
FIGS. 17, 18 and 19 illustrate the effect of endogenous substances with whole plasma, plasma dialysate and macromolecule residual from the dialysis of plasma in glucose fuel cells repectively.
Figure 18:
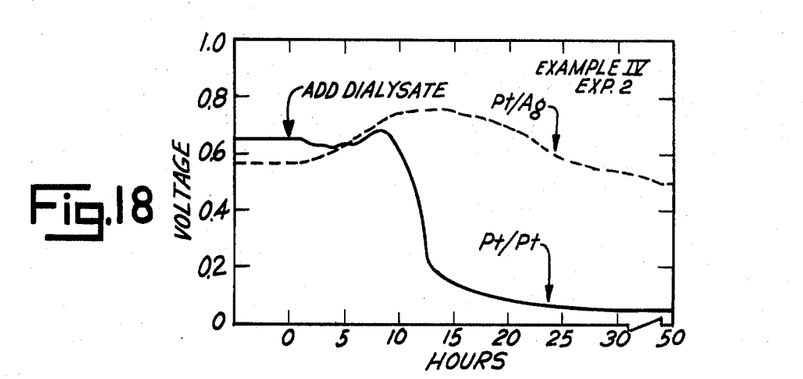
Figure 19:
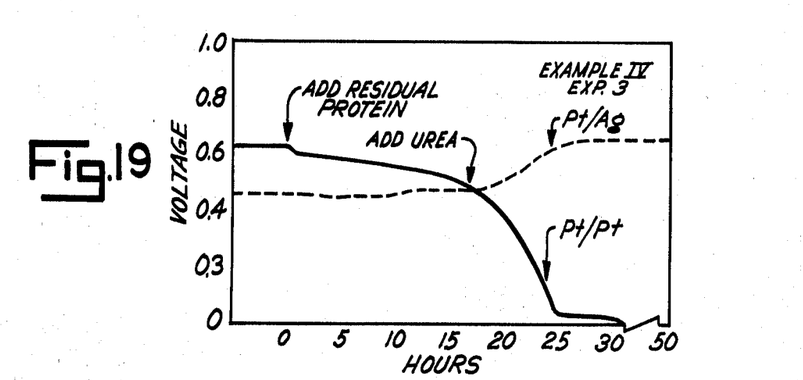

A study of the effect of substances in human plasma was carried out with both Pt/Pt and Pt/Ag sandwich type cells at 37° C. Table 1 is a partial list of the substances present. The plasma and plasma dialysate contained many other usual substances which were not analyzed, and are not listed since conventionally present in plasma or dialysate. Experiments were performed on solutions of the whole plasma, plasma dialysate and the macromolecule residual from the dialysis of the plasma. Results of the three experiments are illustrated in FIGS. 17, 18 and 19 respectively. It was observed that during the 10 hours after addition of the whole plasma or the dialysate to the glucose fuel cells operating under 10 K ohm load, the voltage of the Pt/Ag cells rose steadily and that of the Pt/Pt cells was sway-backed, dipping initially, and then rising above initial voltage values. The voltage of the Pt/Pt cells soon reached a maximum and then relatively quickly (in a few hours) fell to zero. On the other hand, the performance of the Pt/Ag cells shows no such adverse effect. In the Pt/Ag cells, the voltage also fell somewhat after the maximum was reached, but at a lower rate, and the cells also attained a relatively constant level of voltage (or power output). In contrast, the Pt/Pt cells declined to substantially zero.

We discovered that urea was causing the enhancement of operating voltage. Thus, in the third experiment of this series (macromolecule residual), the Pt/Pt and Pt/Ag cells were operated for 17 hours in a buffer solution containing 1.2g % residual protein and 154 mg % glucose but no urea (see FIG. 19). By this time a relatively constant voltage had been reached. 4.0 mg % urea (same concentration as that of the dialsyate experiment) was then added to each cell. The Pt/Pt cell voltage fell rapidly to zero while the Pt/Ag cell voltage rose steadily from 0.46 v to a maximum of 0.64 v within 12 hours. The operating voltage of this cell stayed constant at 0.64 v with a power output of 41μ watts for at least 30 hours before the cell was terminated. This shows the ability of the cells of this invention to utilize, and thereby detoxify, urea, as is expected from the discussion above on deammonation. The urea-poisoned Pt/Pt cells were taken out and soaked in water overnight before they were reimmersed in fresh glucose buffer. These cells were found to be regenerable.

In its broadest aspect, the invention thus involves the use of electrochemical cells in the manner of artificial organs to detoxify toxic substances the body is unable to metabolize. In addition to ammonia and urea, uric acic, creatinine, alanine, drugs such as digitalis glycosides or barbiturates, and toxic agents such as methanol and ethanol may be oxidized to nontoxic products such as $N_2$, $H_2O$, acetate and $CO_2$. Diabetic acidosis could be improved by oxidizing ketone bodies and aceto acetate to $CO_2$ and water. This method will detoxify or eliminate any substance which is oxidizable to harmless or less harmful products and which can be selectively or non-selectively admitted to the anode by means of specific or non-specific covering membranes. The anode itself may also be selective with respect to the toxic substance to be eliminated.

It should be understood that various modifications can be made without departing from the spirit of the invention, and the scope thereof determined by the appended claims which should be interpreted as broadly as the prior art will permit, and in the light of the specification if need be.

We claim:
1. A biomedical device comprising an electro-chemical detoxification cell system which includes:
    a. Cell portion comprising:
        1. a first, oxygen permeable membrane, adapted to have a fluid containing oxygen in contact therewith,
        2. a hydrophobic cathode assembly in association with said oxygen permeable membrane, said cathode assembly being adapted to electrochemically reduce oxygen transferred thereto through said oxygen permeable membrane to OH⁻ ions,
        3. a second membrane adapted to permit transfer therethrough of oxidizable toxic substances present in the extracellular fluid of a patient having endogenous or exogenous toxemia, said extracellular fluid being from at least one natural body fluid zone selected from the circulatory system, the pericardial sac, the abdominal peritoneum, the pleural cavity, the subarachnoid space, and intratissue regions, and which toxic substances said patient's body is unable to properly or promptly metabolize or remove to substantially non-toxic levels,
        4. an anode assembly in association with said second membrane, said anode assembly being adapted to electrochemically oxidize said toxic substances to non-toxic or metabolizable substances,
        5. an ion transfer member disposed between and in intimate association with said cathode and anode assemblies for transfer of ions to said anode assembly,
    b. An electrical circuit portion connected to and disposed external to said cell being adapted to transfer electrons produced at said anode to said cathode assembly, and
    c. Said cell portion being adapted to electrochemically detoxify said toxic substances, and permit return of said fluids to said zones.
2. An electrochemical detoxification cell system of claim 1 in which said circuit is adapted to dissipate electrical energy produced by oxidation of toxic substances in said cell portion.
3. An electrochemical detoxification cell system as in claim 1 wherein:
    a. Said oxygen permeable membrane is selected from a silicone rubber, polycarbonate, polyfluorocarbon and copolymers thereof,
    b. Said second membrane is selected from a cation exchange membrane, a silicone rubber, a polycarbonate, a polyfluorocarbon and copolymers thereof,
    c. Said ion transfer member is selected from a porous inorganic matrix and an anion exchange membrane, and
    d. Said anode assembly includes an anode selected from a hydrophobic and a hydrophilic catalyst material.

4. An electrochemical detoxification cell system as in claim 3 wherein:
   a. Said oxygen permeable membrane is silicone rubber,
   b. Said second membrane is cellulose,
   c. Said ion transfer member is a quaternary ammonium anion exchange membrane, and
   d. Said anode is a hydrophilic catalyst material.

5. An electrochemical detoxification cell system as in claim 3 wherein:
   a. Said oxygen permeable membrane is silicone rubber,
   b. Said second membrane is a cation exchange membrane,
   c. Said ion transfer member is an anion exchange membrane, and
   d. Said anode is a hydrophilic catalyst material.

6. An electrochemical detoxification cell system as in claim 3 wherein:
   a. Both said membranes are silicone rubber,
   b. Said ion transfer member is a porous inorganic matrix, and
   c. Said anode is a hydrophobic catalyst material.

7. An electrochemical detoxification system as in claim 1 which is adapted to be totally internally implanted in an animal body by having a coating or housing of a physiologically compatible material, said coating or housing being adapted to permit exposure of said membranes to body fluids, and the shape of said cell is adapted to conform to the body site wherein implanted.

8. A system as in claim 7 wherein said material is selected from a silicone rubber and a polyfluorocarbon.

9. A system as in claim 4 which is adapted to be totally internally implanted in an animal body by having a coating or housing of a physiologically compatible material, said coating or housing being adapted to permit exposure of said membranes to body fluids, and the shape of said cell is adapted to conform to the body site wherein implanted.

10. A system as in claim 9 wherein said material is selected from silicone rubber and a polyfluorocarbon plastic.

11. A system as in claim 2 wherein said electrical circuit includes means for dissipation of said energy.

12. A system as in claim 11 which includes a power source in said circuit selected from a rechargeable secondary cell and a glucose bioautofuel cell.

13. A system as in claim 12 wherein said power source is a rechargeable secondary cell, and which includes switch means adapted to selectively permit said electrochemical cell portion to charge said secondary cell in a first switched mode when said toxic substance concentration is high, and to permit said secondary cell to provide current to said electrochemical cell portion in a second switched mode when said toxic substance concentration is low.

14. A system as in claim 1 which includes means for passing blood through an extracorporeal shunt from and to an animal body, and wherein said cell system is disposed in association with said shunt to expose said second membrane to said blood passing therethrough.

15. A system as in claim 14 which includes means for passing oxygen or air into association with said first membrane.

16. A system as in claim 14 wherein said electrical circuit includes a DC power source to provide energy to said electrochemical cell to increase the rate of toxic substance oxidation in said electrochemical cell.

17. A system as in claim 16 which includes a plurality of said electrochemical cell portions electrically connected in parallel.

18. A system as in claim 1 wherein said cathode includes a high surface area metal consisting essentially of silver and said anode includes a high surface area metal comprising platinum.

19. A biomedical device as in claim 1 which includes:
   d. means for passing said extracellular fluid through an extracorporeal shunt from and to the body of said patient,
   e. a dialyzer unit associated with said shunt,
      1. said dialyzer containing a membrane in contact with said extracellular fluid,
      2. said dialyzer membrane being adapted to permit the passage therethrough of said toxic substances from said extracellular fluid to a dialysis fluid, and
   f. said second membrane is in contact with said dialysis fluid containing said toxic substances.

20. A biomedical device as in claim 19 wherein said extracellular fluid is blood.

21. A biomedical device as in claim 19 which includes means for passing a gas containing oxygen into association with said first membrane.

22. A biomedical device as in claim 19 wherein said electrical circuit includes a DC power source to provide energy to said electrochemical cell to increase the rate of toxic substance oxidation in said electrochemical cell.

23. A biomedical device as in claim 19 wherein:
   Said oxygen permeable membrane is selected from a silicone rubber, a polycarbonate, a polyfluorocarbon and copolymers thereof,
   b. Said second membrane is selected from a cation exchange membrane, a silicone rubber, a polycarbonate, a polyfluorocarbon and copolymers thereof,
   c. Said ion transfer member is selected from a porous inorganic matrix and an anion exchange membrane, and
   d. Said anode assembly includes an anode selected from a hydrophobic and a hydrophilic catalyst material.

24. A biomedical device as in claim 23 wherein:
   a. Said oxygen permeable membrane is silicone rubber,
   b. Said second membrane is cellulose,
   c. Said ion transfer member is a quarternary ammonium anion exchange membrane, and
   d. Said anode is a hydrophilic catalyst material.

25. A biomedical device as in claim 23 wherein:
   a. Said oxygen permeable membrane is silicone rubber,
   b. Said second membrane is a cation exchange membrane,
   c. Said ion transfer member is an anion exchange membrane, and
   d. Said anode is a hydrophilic catalyst material.

26. A biomedical device as in claim 23 wherein:
   a. Both said membranes are silicone rubber,
   b. Said ion transfer member is a porous inorganic matrix, and
   c. Said anode is a hydrophobic catalyst material.

27. A biomedical device as in claim 3 which includes:
   a. A power source in said circuit, and
   b. Switch means adapted to provide current from said power source to said electrochemical cell portion when said toxic substance concentration is low.

* * * * *

UNITED STATES PATENT AND TRADEMARK OFFICE
CERTIFICATE OF CORRECTION

PATENT NO. : 3,994,799  
DATED : November 30, 1976  
INVENTOR(S) : Yao et al.

Page 1 of 2

It is certified that error appears in the above-identified patent and that said Letters Patent are hereby corrected as shown below:

Abstract, line 31, "27 Claims, 20 Drawing Figures" should read --27 Claims, 19 Drawing Figures--.

Column 1, line 32, "diseses" should read --diseases--.

Column 1, line 37, "hemedialysis" should read --hemodialysis--.

Column 1, line 59, "P.M." should read --P.M.,--.

Column 1, line 65, "System" should read --System,--.

Column 4, line 39, "nepatic" should read --hepatic--.

Column 4, line 41, "implantble" should read --implantable--.

Column 4, line 42, "Wolfsor" should read --Wolfson--.

Column 7, line 38, "exchanger" should read --exchange--.

Column 7, line 43, "$OH^+$" should read --$OH^-$--.

Column 7, line 51, "$OH^+$" should read --$OH^-$--.

Column 10, line 40, "metalbolites" should read --metabolites--.

Column 10, line 40, "currnet" should read --current--.

Column 10, line 42, "dialysateurea" should read --dialysate-urea--.

Column 10, line 43, "shch" should read --such--.

Column 10, line 47, "Fig. 14" should read --Fig. 13--.

UNITED STATES PATENT AND TRADEMARK OFFICE
CERTIFICATE OF CORRECTION

PATENT NO. : 3,994,799
DATED : November 30, 1976
INVENTOR(S) : Yao et al.

It is certified that error appears in the above-identified patent and that said Letters Patent are hereby corrected as shown below:

Column 11, line 18, "medidal" should read --medical--.

Column 11, line 45, "glucoseurea" should read --glucose-urea--.

Column 12, line 9, "area" should read --urea--.

Column 12, line 26, "AMFion" should read --AMF ion--.

Column 12, line 63, "$CO_2$." should read --$CO_2$,--.

Column 13, line 63, "charged" should read --changed--.

Column 14, line 34, "0.0008" should read --0.008 inch--.

Column 15, line 13, "5 mN" should read --5 mM--.

Column 16, line 11, "NOne" should read --None--.

Signed and Sealed this twelfth Day of July 1977

[SEAL]

Attest:

RUTH C. MASON
Attesting Officer

C. MARSHALL DANN
Commissioner of Patents and Trademarks